(12) United States Patent
Shimada

(10) Patent No.: US 7,325,925 B1
(45) Date of Patent: Feb. 5, 2008

(54) PERIMETER

(75) Inventor: Satoshi Shimada, Hamamatsu (JP)

(73) Assignee: Kowa Company, Ltd., Aichi (JP)

( * ) Notice: Subject to any disclaimer, the term of this patent is extended or adjusted under 35 U.S.C. 154(b) by 0 days.

(21) Appl. No.: 11/683,632

(22) Filed: Mar. 8, 2007

(30) Foreign Application Priority Data

Aug. 9, 2006 (JP) .............................. 2006-217452

(51) Int. Cl.
*A61B 3/14* (2006.01)
*A61B 3/02* (2006.01)

(52) U.S. Cl. ...................................... 351/206; 224/226

(58) Field of Classification Search ................ 351/224, 351/226, 211, 200–206, 237, 243, 245

See application file for complete search history.

(56) References Cited

U.S. PATENT DOCUMENTS 4,679,920 A * 7/1987 Takashi et al. ............. 351/226
6,318,860 B1 * 11/2001 Suzumura ................... 351/224
7,244,027 B2 * 7/2007 Sumiya ...................... 351/224

FOREIGN PATENT DOCUMENTS

JP 60-241419 11/1985
JP 2000-262472 9/2000

\* cited by examiner

*Primary Examiner*—M. Hasan
(74) *Attorney, Agent, or Firm*—Duane Morris LLP

(57) ABSTRACT

A Perimeter is provided for designating a perimetry point for an eye to be examined with a fundus image of the eye which has already been provided so as to compensate the individual variation in the position of a blind spot to the maculalutea.

2 Claims, 10 Drawing Sheets

FIG. 8
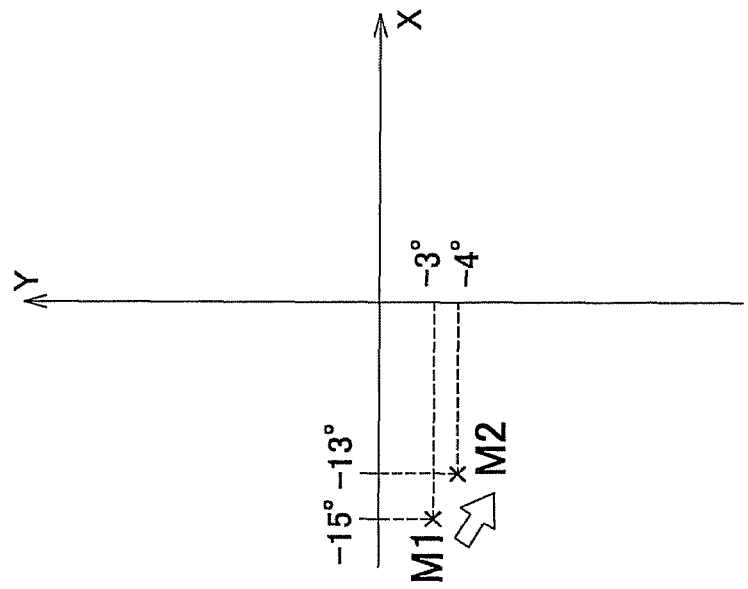
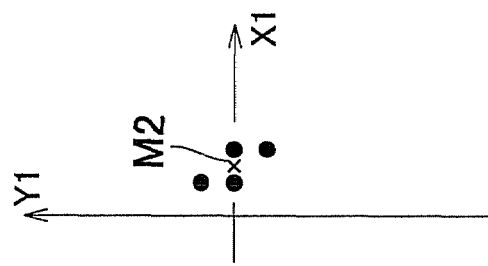
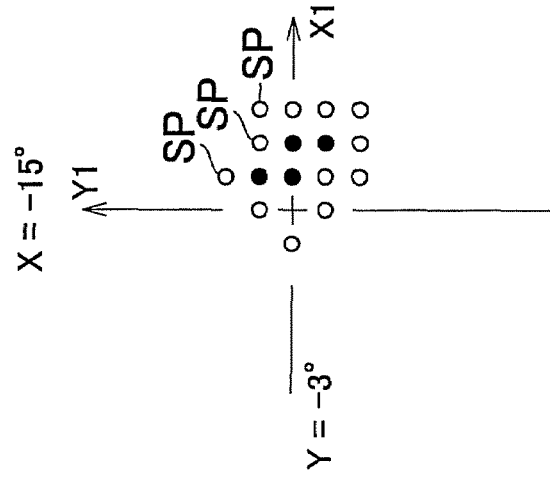

FIG. 10
(a)
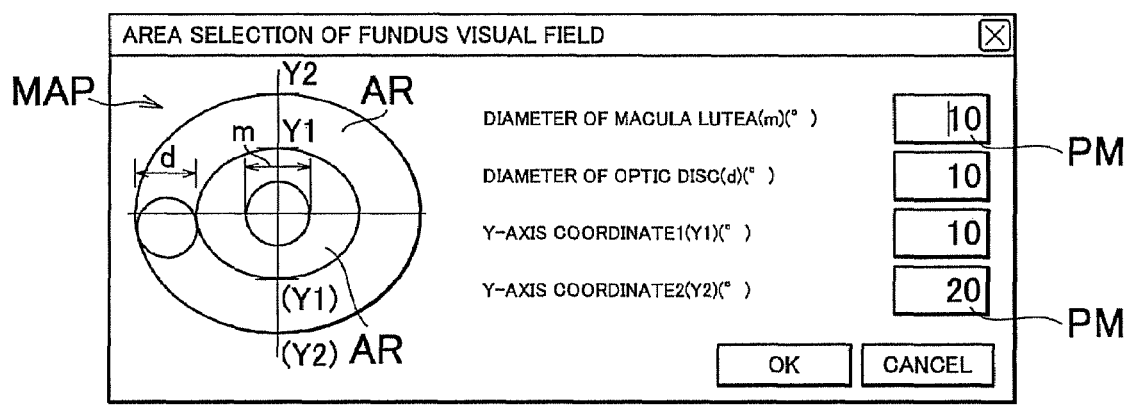
(b)
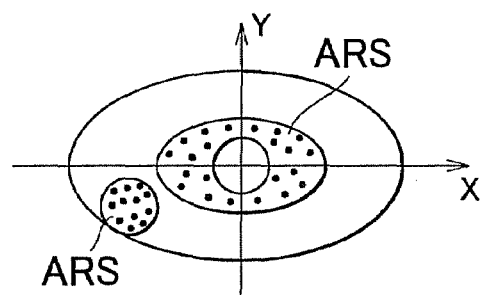

PERIMETER

BACKGROUND OF THE INVENTION

This invention relates to a perimeter for designating a perimetry point for an eye to be examined with a fundus image of the eye which has already been photographed.

BACKGROUND ART

The technique of designating a perimetry point for an eye to be examined with a fundus image of the eye which has already been photographed in a perimetry is already known from a patent application publication number of which is 2000-262472, for instance.

In such a case, it is necessary to correctly correspond, a coordinate on the image of the examined eye which is shown on the fundus image, and an actual coordinate of the eye on which a perimetry will be conducted from now on with each other. Generally, a X-Y coordinate system is set for the fundus image provided that a position of a blind spot on the fundus image is a predetermined coordinate position with respect to a macula lutea (a central portion of the visual field), X=−15° and Y=−3°, for instance. But, it is impossible to conduct the correct perimetry as long as some coordinate correction is not executed since there is an individual variation in the position of the blind spot with respect to the macula lutea.

Then, the object of the invention is to provide a perimeter for correctly conducting a perimetry by setting a coordinate system on the fundus image so as to compensate the individual variation in the position of the blind spot to the macula lutea in order to solve the above-mentioned inconvenience.

SUMMARY OF THE INVENTION

One aspect of the invention is perimeter for perimetry on an eye to be examined by presenting a stimulus at a predetermined coordinate position of a first visual field coordinate system which is set on a visual field dome, comprising:

a memory for storing a fundus image of said eye to be examined;

means to control display for reading said fundus image and displaying said fundus image on a monitor;

means to set coordinate for setting a second visual field coordinate system wherein a macula lutea portion of said fundus image which is displayed on said monitor is an origin on said fundus image displayed on said monitor;

means for provisionally determining blind spot coordinate, for provisionally determining a blind spot position on said fundus image on said second visual field coordinate system;

means to search blind spot for searching a coordinate position of a blind spot of said eye to be examined on said first visual field coordinate system by presenting said stimulus to said eye to be examined on said visual field dome;

means to change scale for changing a scale of said second visual field coordinate system so as to correspond said coordinate value of said blind spot of said eye to be examined on said first visual field coordinate system which is obtained by said means to search blind spot and said coordinate value of said blind spot of said fundus image on said second visual field coordinate system with each other; and means to conduct perimetry for conducting a perimetry on said eye to be examined by presenting said stimulus on said visual field dome at a position on said first visual field coordinate system having the same coordinate value as one on said second coordinate system of a predetermined test point on said fundus image.

The other aspect of the invention is the perimeter, wherein further comprising a memory for storing standard blind spot position coordinate data showing positions where blind spots generally exist, and means to control search for controlling said means to search blind spot to read said standard blind spot position coordinate data from said memory and to search said blind spot at a periphery of said coordinate position which is shown in said standard blind spot position coordinate data when said means to search blind spot searches said coordinate position of said blind spot on said first visual field system.

According to both aspects of the invention, the scale of the second visual field coordinate system which is set on the fundus image and the scale of the first visual field coordinate system which is set on the visual field dome can be correctly corresponded with each other so as to compensate an individual variation in the position of the blind spot to the macula lutea, and the perimetry on an eye to be examined can be correctly conducted by designating the test point on the fundus image.

BRIEF DESCRIPTION OF THE DRAWINGS

FIG. 8 is a view showing an instance of the fundus image which is displayed on the monitor of the perimeter for showing one of a series of perimetry routines.

FIG. 10 is a view showing an input screen to be used when instructing an area on which perimetry is conducted and a set area.

DESCRIPTION OF THE PREFERRED EMBODIMENTS

An embodiment of the invention will now be explained, referring to appended figures.

Figure 1:
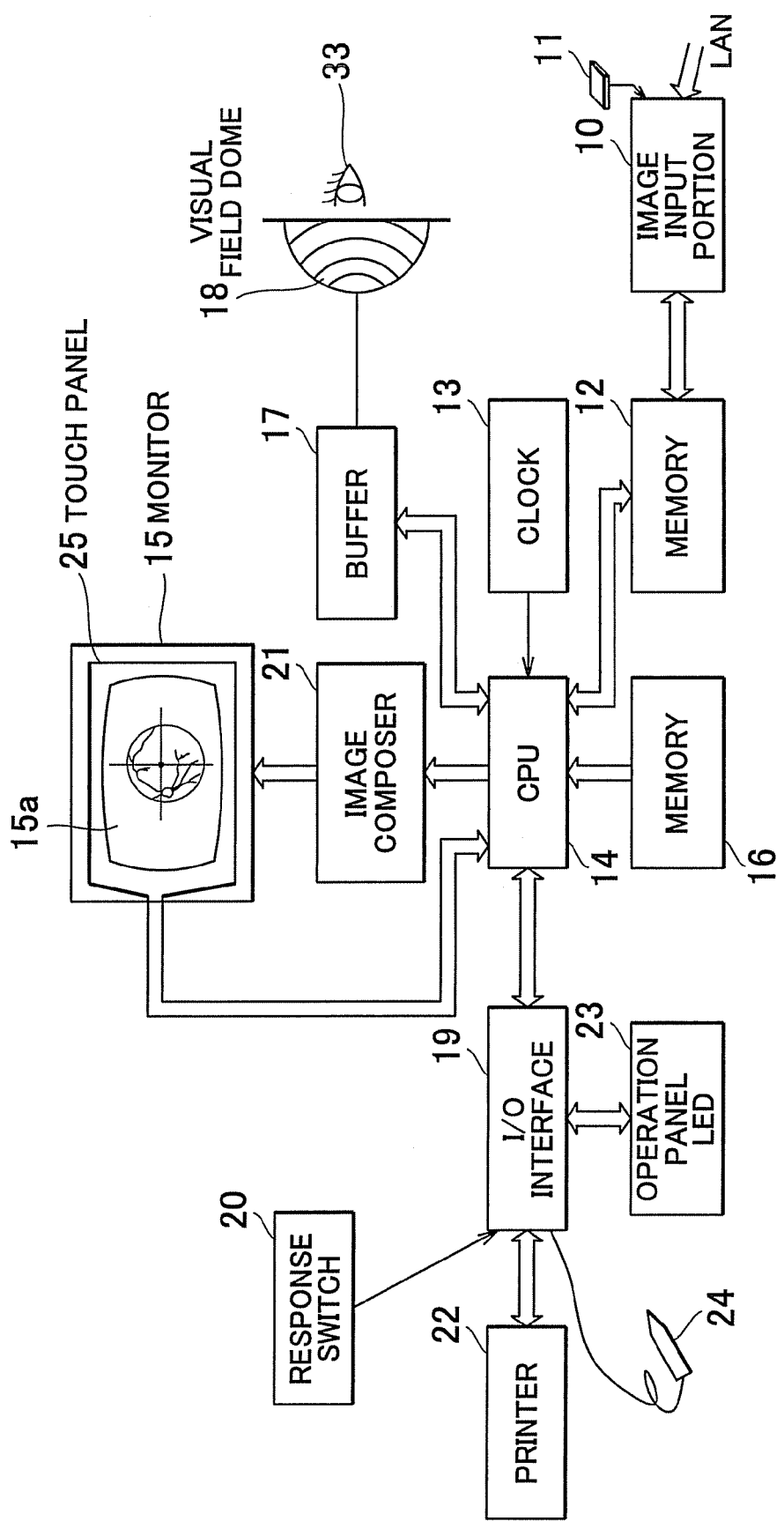
FIG. 1 is a block diagram showing an instance of a perimeter.

FIG. 1 is a block diagram showing an instance of a perimeter, FIGS. 2 through 9 are views respectively showing an instance of a fundus image which is displayed on a monitor of a perimeter showing a series of perimetry routines, and FIG. 10 is a view showing an input screen to be used when instructing an area on which perimetry is conducted and an instance of a set area.

A reference numeral 10 of FIG. 1 denotes an image input portion, into which electrically imaged fundus data is inputted through a removable disc, such as a floppy disc 11 or a CD, or from a LAN. A fundus image is stored in the floppy disc 11 or is transmitted through a LAN after taking by a fundus camera (not shown) through a television camera (a CCD camera) and executing image processing thereon. The fundus image which is inputted into the image input portion 10 can be displayed on a display portion, such as a monitor 15, through a CPU 14 operating so as to synchronize with a clock 13 after storing in a memory 12.

And, a program for perimetry is stored in a memory 16, and as mentioned hereinafter, the CPU 14 displays stimuli in order on a visual field dome 18 through a buffer 17 when designating a predetermined area of a fundus which is displayed on the monitor 15. On this occasion, the stimuli are displayed by projecting on the visual field dome or lighting a light source which is located on the visual field dome, such as a LED. The stimuli are displayed in connection with the designated fundus area, and the displayed stimulus is formed at the designated area on the fundus when an examinee fixates a center of the visual field dome.

An Examinee responds through a response switch 20 when perceiving the stimulus displayed on the visual field dome 18, and this response is transmitted to the CPU 14 through an I/O interface 19. The CPU 14 can display on the monitor 15 an image on which the image processed by the CPU 14 is synthesized through an image composer 21.

And, an operation panel 23 having a light source, such as a LED, is connected with the I/O interface 19, and through the operation panel 23, various kinds of operations, such as image input, perimetry and image synthesis, can be designated, and these operations can be transmitted to the CPU 14 through the I/O interface 19. Besides, a measurement result or the image displayed on the monitor 15 can be outputted to a printer 22 through the I/O interface 19. It is possible to set or designate the area of the image displayed on the monitor 15 with a light pen 24 through a touch panel 25 which is located on the monitor 15.

Subsequently, the fundus image data is inputted into the image input portion 10 through the floppy disc or the LAN, and is stored in the memory 12, and thereafter, the fundus image is displayed on the monitor 15 through the CPU 14 in such a structure. This state is shown in FIG. 2, which shows that a fundus image 30 is displayed on a screen 15a of the monitor.

An examinee is invited to fixate the stimulus projected on a projection plane inside the visual field dome 18, and responds to an examiner through an appropriate method, such as operation of the response switch 20 and response by voice when perceiving the stimulus.

Figure 2:
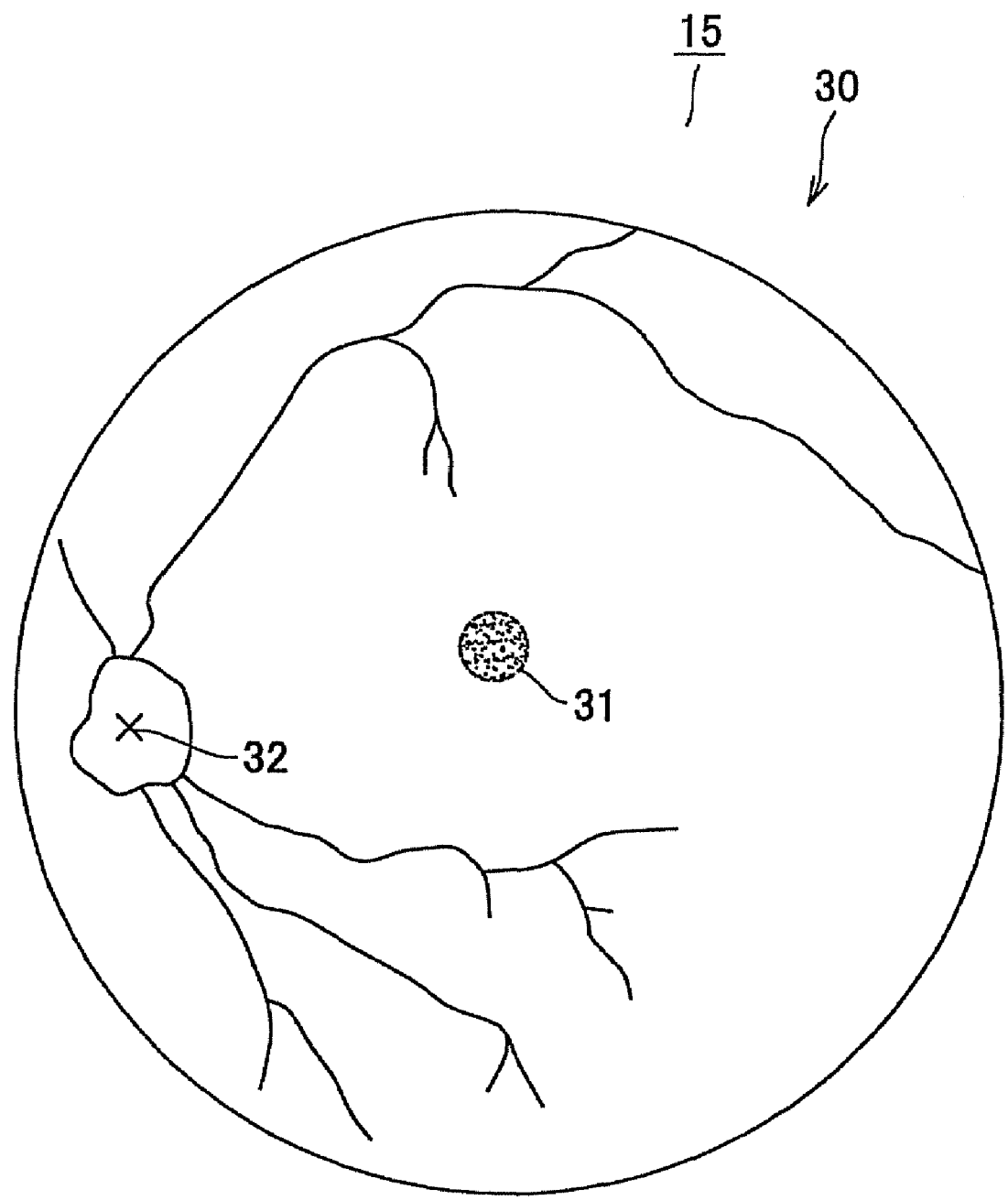
FIG. 2 is a view showing an instance of a fundus image which is displayed on a monitor of a perimeter for showing one of a series of perimetry routines.
Figure 3:
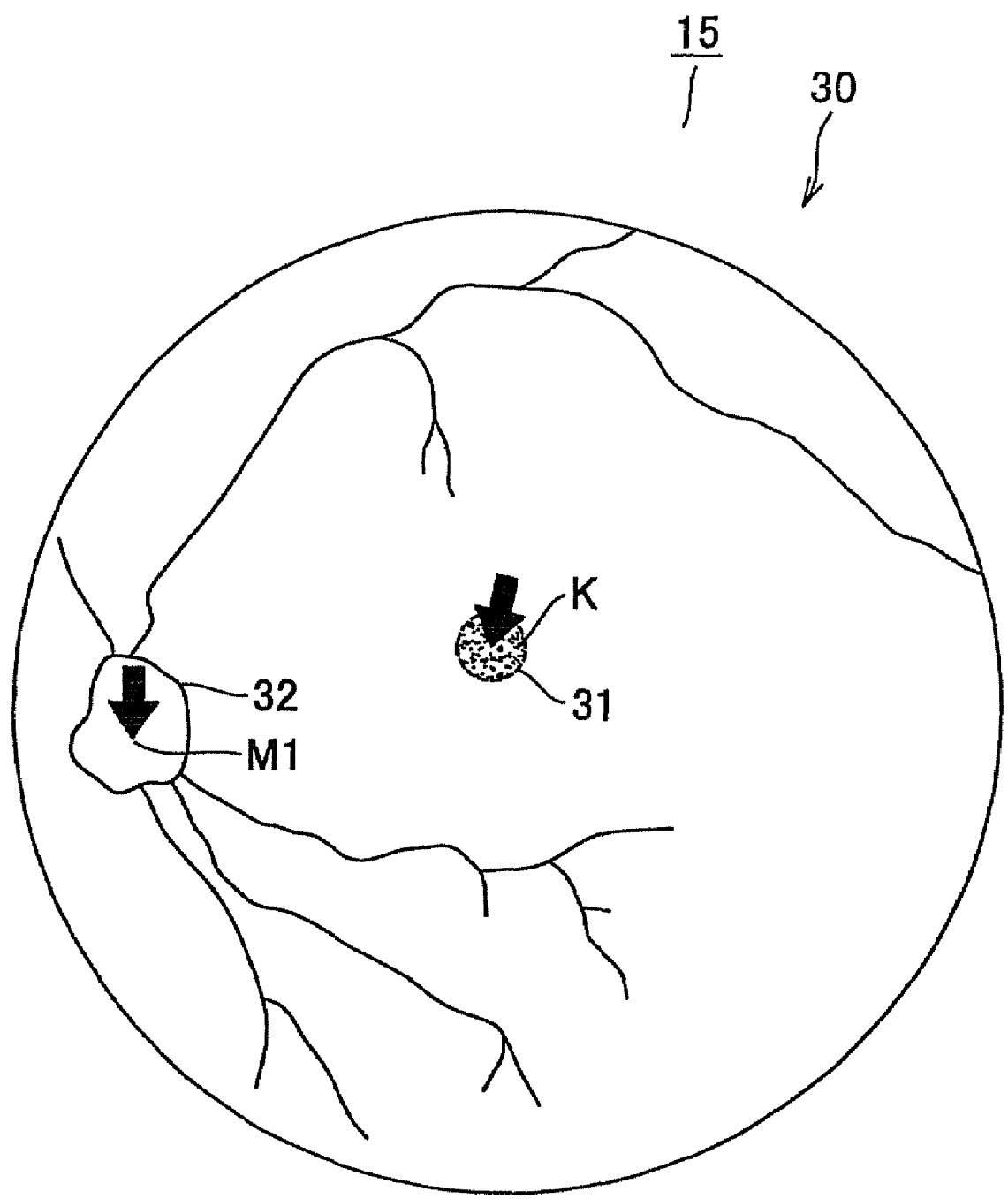
FIG. 3 is a view showing an instance of the fundus image which is displayed on the monitor of the perimeter for showing one of a series of perimetry routines.

As shown in FIG. 2, the fundus image 30 is displayed on the monitor 15. The fundus image 30 is displayed reversely in an up/down direction so as to match with perimetry in comparison with normal display of a fundus image. In the above-mentioned state, the examiner designates a center of a macula lutea position K which is a center of a macula lutea portion 31 as a center of the visual field (origin ZP) on the fundus image 30 displayed on the monitor 15 with the light pen 24 as shown in FIG. 3, and furthermore designates a central position of a blind spot (optic disc) 32 as a blind spot position M1.

Figure 4:
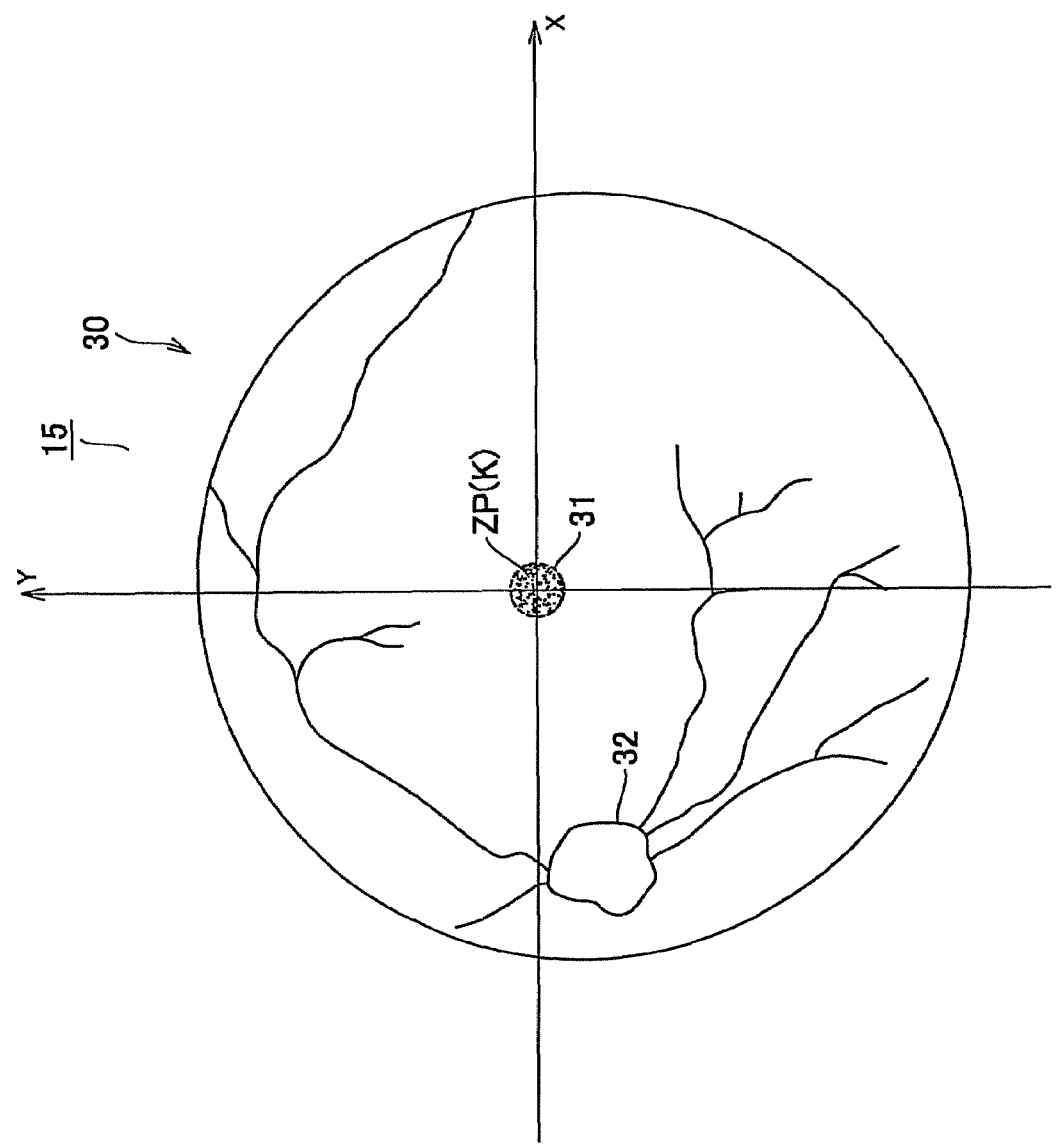
FIG. 4 is a view showing an instance of the fundus image which is displayed on the monitor of the perimeter for showing one of a series of perimetry routines.
Figure 5:
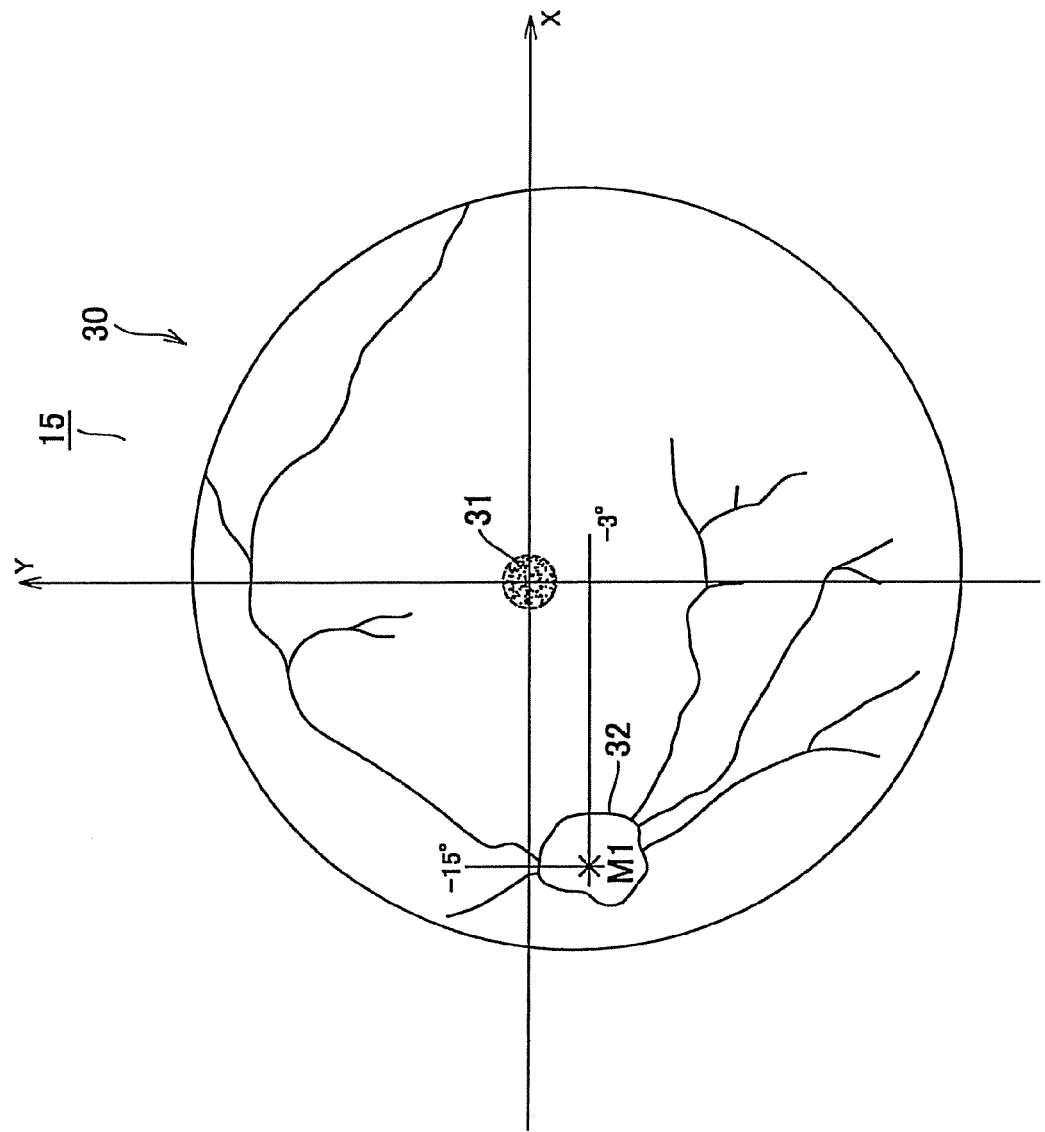
FIG. 5 is a view showing an instance of the fundus image which is displayed on the monitor of the perimeter for showing one of a series of perimetry routines.

The CPU 14 detects and computes coordinate positions of the macula lutea position K and the blind spot position M1 on the monitor 15 which are shown with the light pen 24 on the basis of perimetry program stored in the memory 16, and sets a X-Y coordinate system which origin is the macula lutea portion 31, as shown in FIG. 4. Subsequently, the CPU 14 provisionally determines the blind spot position M1 which has been designated by the examinee on the monitor as X=−15° and Y=−3° on the basis of standard blind spot position coordinate data (which are detailedly mentioned hereinafter) which is generally (statistically) considered to be the blind spot position coordinate on the macula lutea portion 31 as shown in FIG. 5 according to the perimetry program, and a scale of the X-Y coordinate is corresponded to the blind spot position M1, and is displayed on the fundus image.

Figure 6:
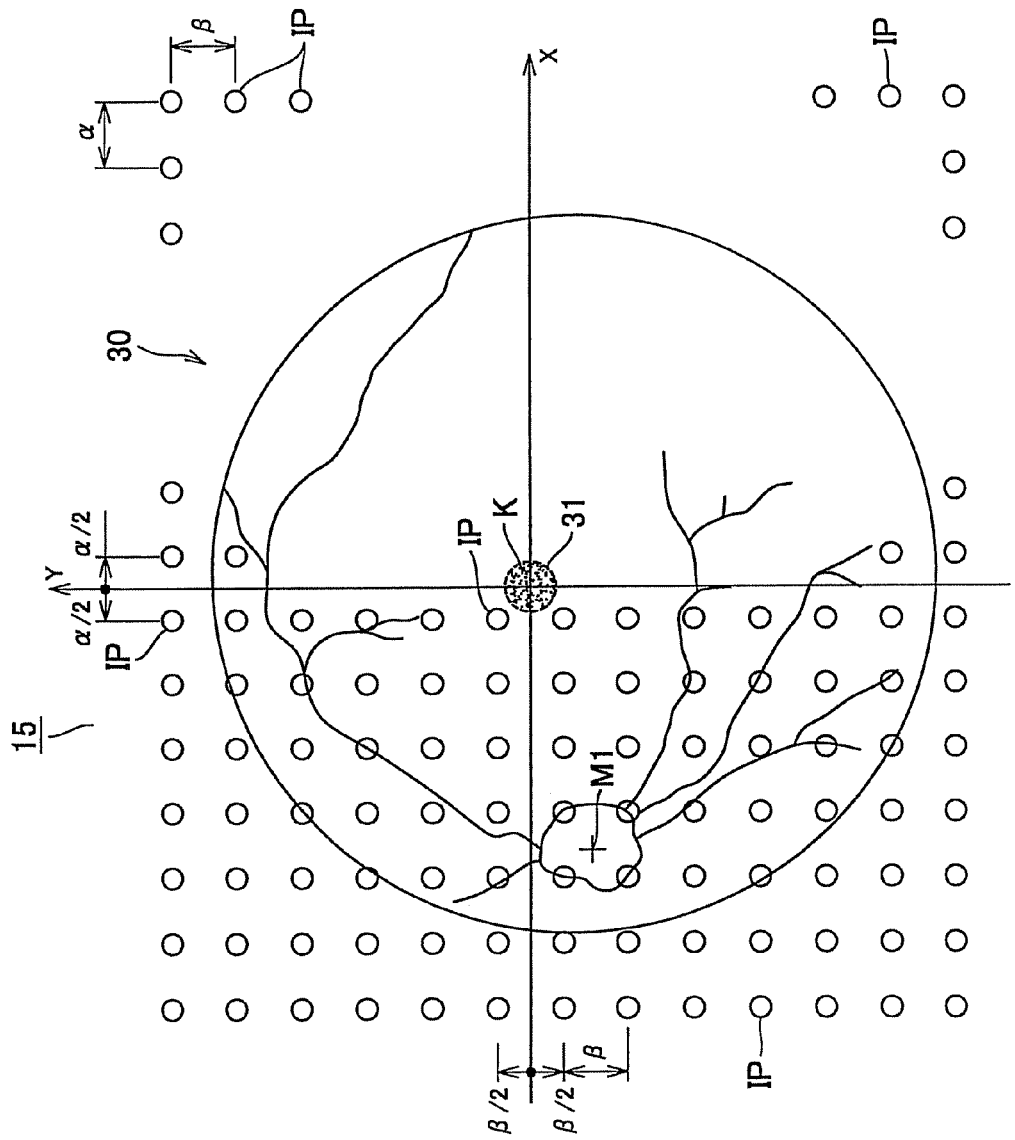
FIG. 6 is a view showing an instance of the fundus image which is displayed on the monitor of the perimeter for showing one of a series of perimetry routines.
Figure 7:
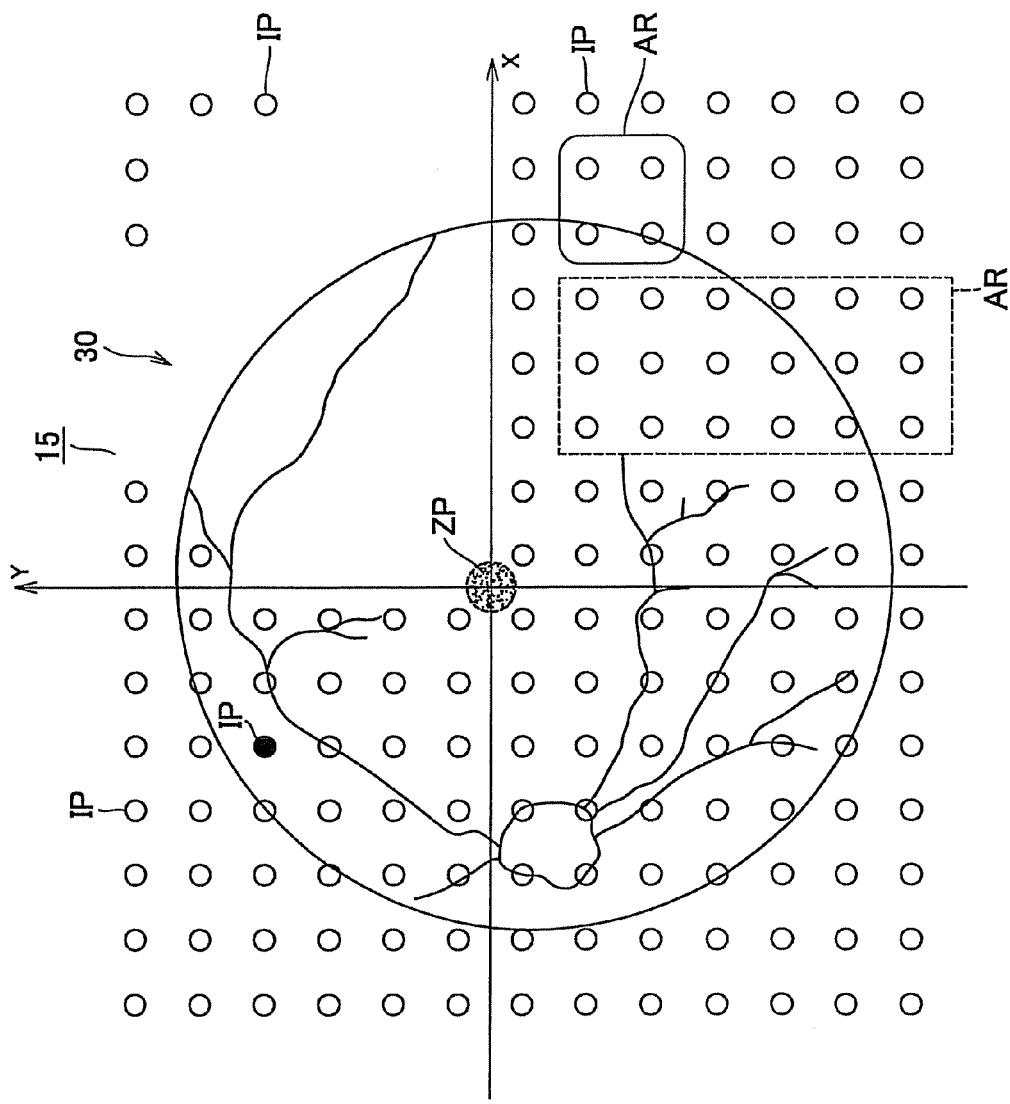
FIG. 7 is a view showing an instance of the fundus image which is displayed on the monitor of the perimeter for showing one of a series of perimetry routines.

Subsequently, the CPU 14 displays a measurement point which is set in advance, that is, a test point IP on the monitor as shown in FIG. 6 according to the perimetry program. The test points IP displayed in FIG. 6 are set with visual field angles $\alpha$ and $\beta$ in the X-axis and Y-axis directions. Concretely speaking, the test points IP are equally allotted at intervals of $\alpha$, $\beta$ in the X-axis and Y-axis directions in such a way that the points are distributed respectively separated from the X- and Y-coordinate axes by $\alpha/2$ and $\beta/2$. Although the set angles of $\alpha$ and $\beta$ are optional, the set angles are 4° through 5°, for instance.

When using an insertion lens for an eyepiece (not shown) into which an examinee for perimetry looks for the reason of a visual acuity grade, an examiner inputs a correcting value of the insertion lens through the operation panel 23, and the CPU 14 adjusts the scale of the X-Y coordinate on the fundus image 30 according to the inputted correcting value of the insertion lens in order to correct the coordinate axis. If the insertion lens is inserted, the position on the visual field dome 18 at which an examinee perceives may shift 20 percent due to prism effect of the insertion lens, for instance. In such a case, the scale of the X-Y coordinate on the fundus image 30 is corrected according to the shift amount.

When instructing the coordinate position on the fundus image 30 in the above-mentioned state, it is possible to correspond to an examined eye 33 which looks onto the corresponding visual field dome 18 to the visual field coordinate on the visual field dome 18 to each other in appearance. If the position of the stimulus to be presented (corresponding to the test point IP) is displayed on the visual field dome 18, designating the visual angle of the X-Y coordinate on the basis of the scale which is set on the X-Y coordinate on the fundus image 30 displayed on the monitor 15, but, an error occurs between the position of the stimulus on the fundus image 30 (corresponding to the test point IP) and the actual position of the stimulus which is presented to the examined eye in the visual field dome 18 since a positional relation between the macula lutea position K and the blind spot position M1 is actually different due to individual variation.

On the other hand, an examiner designates a point on which perimetry is executed for the examined eye 33 from now on, on the screen of the monitor 15 with the light pen 24 or the like on the basis of the fundus image 30 and the image of the test points IP which are displayed on the monitor 15 by individually designating the image of the test point IP (the test point IP shown with a black spot of FIG. 7, for instance) or designating an area AR including two or more test points IP to be examined. The test point(s) IP to be examined can be designated, directly confirming the fundus image 30 of the examined eye 33 on the monitor 15, thereby easily selecting the test point(s) IP which is proper for the state of the examined eye 33.

Various methods are considered in order to designate the test point(s) IP. For instance, the CPU 14 may read an area selection map MAP having two or more divided areas AR which should be designated for perimetry on the fundus image 30 from the memory 16 according to the perimetry program as shown in FIG. 10(a) and the area may be displayed on the monitor 15, and the examiner may be invited to select the area AR with the light pen 24 or the like.

In such a case, the sizes of the respective areas AR in the area selection map MAP may be set so as to match with a case of disease on the examined eye 33 or the state of the fundus image 30 in such a way that two or more parameters which can be set by the examiner, such as "diameter of macula lutea (m) (°)", "diameter of optic disc(d) (°)", "Y-axis coordinate 1 (Y1) (°)" and "Y-axis coordinate 2 (Y2) (°)" are set as shown in FIG. 10(a), and the examiner can properly input these parameter values PM through the operation panel 23. When thus inputting various kinds of parameters, the CPU 14 transforms the respective areas AR in the area selection map MAP so as to correspond to the inputted parameter values PM, and displays the areas as shown in FIG. 10(b), for instance. In case of FIG. 10(b), the area selection map MAP is formed in an elliptic shape as a whole by designating the parameter values PM, and the test points IP belonging to the area are displayed on the area ARS which is selected by the examiner. Besides, two or more kinds of distribution patterns of the test points IP can be stored in the memory 16 for the test points IP which are arranged on each area ARS so as to select by the examiner. In such a case, the examiner may select the distribution pattern of the test point IP, matching with the case of disease.

When thus selecting the test point IP to be measured, the examiner inputs a measurement start instruction to the CPU 14 through the operation of the operation panel 23. Receiving this instruction, the CPU 14 corrects the scale which is set on the X-Y coordinate displayed on the monitor 15, that is, corrects the coordinate of the blind spot position M1 according to the perimetry program.

Firstly, the CPU 14 starts a processing for searching a blind spot position, for obtaining the actual blind spot position of the examined eye on the X-Y coordinate (first visual field coordinate system) which is set on the visual field dome 18 according to the perimetry program. In this processing for searching a blind spot position, the CPU 14 reads a standard blind spot position coordinate, X=−15' and Y=−3°, which is stored in the memory 16 as the standard blind spot position coordinate data showing a position where the blind spot generally exists. The CPU 14 sets two or more search points SP (a location density of which is higher than one of the test points IP) near the coordinate X=−15°, Y=−3° as shown in FIG. 8(a) on the basis of the read standard blind spot position coordinate X=−15° and Y=−3° on the X-Y coordinate which is set on the visual field dome 18, and presents these set search points SP to the examined eye 33 in order, collects the response states, stores the collected in the memory 16, and displays on the monitor 15.

If the search points SP to which a response of informing of perception of the stimulus is given from the examinee are shown with white spots, and the search points SP to which no response is given from the examinee are shown with black spots as shown in FIG. 8(a), the examinee does not respond to the blind spot portion without the perception of the stimulus. Then, one or more black spots of the blind spot portion, that is, the portions to which no response is give from the examinee, are registered, as shown in FIG. 8(b).

The CPU 14 judges the area where the search points SP receiving no response are arranged to be the actual blind spot of the examined eye 33, and obtains a blind spot position M2 on the X-Y coordinate which is set on the visual field dome 18 by computing a center of gravity or a coordinate average between two or more search points SP receiving no response. If there is only one search point SP to which no response is given, the search point SP is determined as the blind spot position M2. In such a search of the blind spot position, the CPU 14 reads the standard blind spot position coordinate data which is stored in the memory 16 according to the perimetry program, and the search is conducted at a periphery of the coordinate position on the basis of the read standard blind spot position coordinate data, thereby searching the blind spot position in a time much shorter than the random search of the blind spot position on the visual field coordinate system in the visual field dome.

If the coordinate of the blind spot position M2 of the examined eye 33 which was searched on the visual field dome 18 is X=−13° and Y=−4°, for instance, this coordinate value is the correct blind spot position M2 of the examined eye 33. Then, the CPU 14 corrects the scale of the X-Y coordinate (the second visual field coordinate system) set on the fundus image 30 so that the blind spot position M1 (coordinate X=−15° and Y=−3°) on the X-Y coordinate which is the second visual field coordinate system provisionally set on the fundus image 30 can be the coordinate X=−13° and Y=−4° even in the X-Y coordinate on the fundus image 30.

Figure 9:
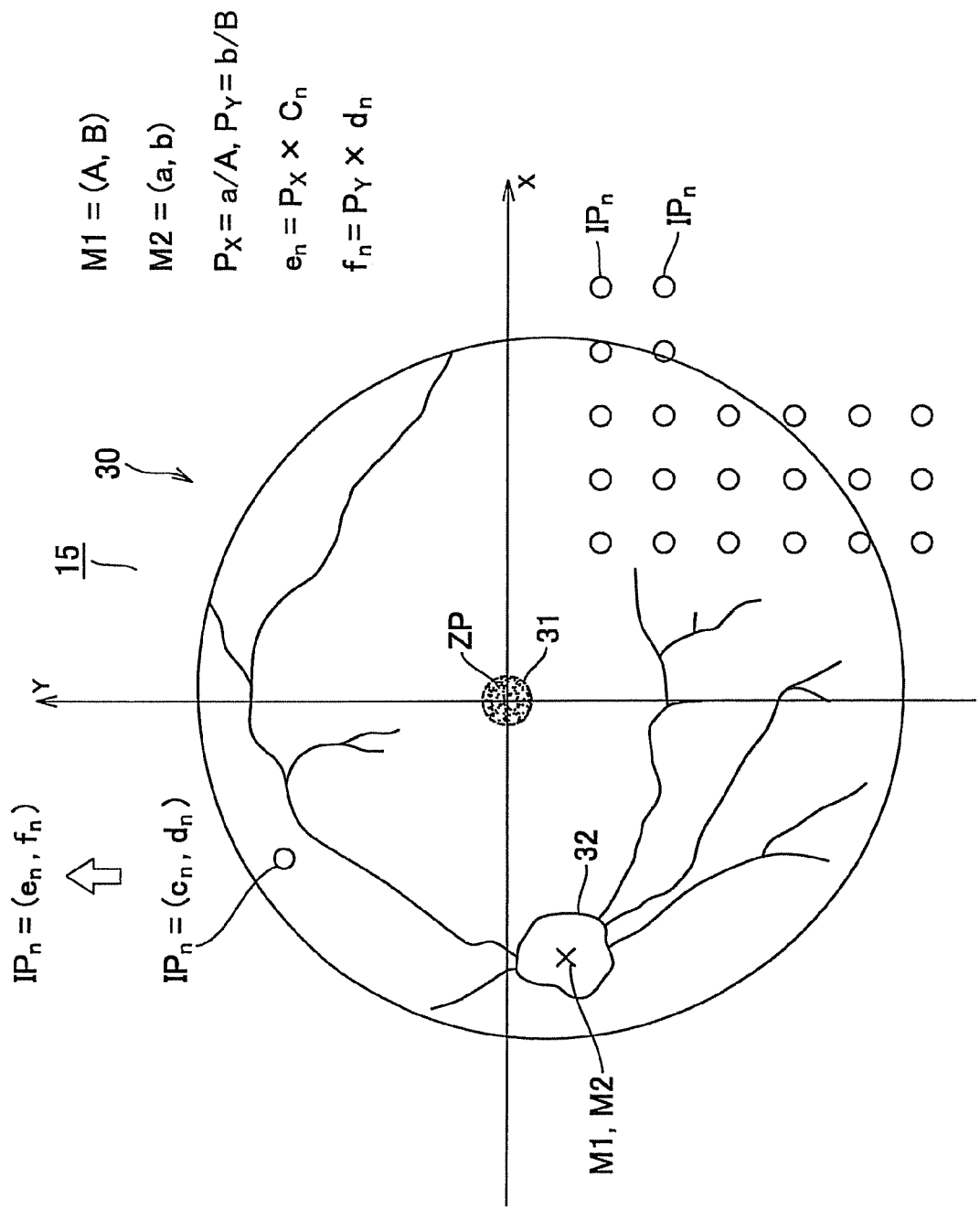
FIG. 9 is a view showing an instance of the fundus image which is displayed on the monitor of the perimeter for showing one of a series of perimetry routines.

In such a case where the blind spot position M1 on the fundus image 30 which is provisionally set is the coordinate (A, B) (in the last instance (X=−15°, Y=−3°) and the blind spot position M2 of the examined eye 33 which has been actually measured is the coordinate (a, b) (in the last instance (X=−13°, Y=−4°), this correction is executed in such a way that the CPU 14 obtains both correction factors, a correction factor for X-axis $P_X$ and a correction factor for Y-axis $P_Y$ from both expressions $P_X=a/A$ and $P_Y=b/B$, and the scale of the X-Y coordinate which is set on the fundus image 30 is multiplied by both correction factors, as shown in FIG. 9. In case of FIG. 9, the blind spot position of the fundus image is changed from M1 (X=−15°, Y=−3°) into M2 (X=−13°, Y=−4°) since $P_X$=−13°/−15°=0.867 and $P_Y$=−4°/−3°=1.33.

Thereafter, the coordinate $IP_n$ ($c_n$, $d_n$) of each search point IP which is displayed on the fundus image 30 is changed into $IP_n$ ($e_n$, $f_n$) wherein $e_n=P_X\times c_n$ and $f_n=P_Y\times d_n$. Then, each position (x, y) on the X-Y coordinate (the second visual field coordinate system) which is set on the fundus image 30 correctly corresponds to the same coordinate value (x, y) on the X-Y coordinate (the first visual field coordinate system) which is set on the visual field dome 18 with one-to-one-correspondence so as to correspond both coordinate values with each other.

After thus correcting the scale of the X-Y coordinate system on the fundus image 30 by the CPU 14, that is, converting the second visual field coordinate system (the X-Y coordinate system) which is set on the fundus image 30 into the first visual field coordinate system (the X-Y coordinate system) which is set on the visual field dome 18, the examiner executes perimetry on the examined eye 33 with the fundus image as a guide.

That is, the test is conducted on the test point IP which is already designated by the examiner by presenting the stimulus having a predetermined luminance at the coordinate position of the visual field dome 18 having the coordinate value the same as one of the test point IP. Since the CPU 14 properly corrected the scale between the second visual field coordinate system which is set on the fundus image 30 and the first visual field coordinate system which is set on the visual field dome 18 as already mentioned, the predetermined test point IP on the fundus image 30 is presented to the examined eye 33 so that the stimulus can be positioned so as to have the positional relation the same as the relative position of the test point IP with respect to the fundus image 30 even in the visual field dome 18. Then, it is possible to correctly present the stimulus to the examined eye 33 which looks into the visual field dome 18 through the fundus image 30.

The invention can be utilized as a perimeter for perimetry by designating the predetermined test point IP with the fundus image and presenting the stimulus at the corresponding position on the visual field dome.

The present invention has been explained on the basis of the example embodiment discussed. Although some variations have been mentioned, the embodiments which are described in the specification are illustrative and not limiting. The scope of the invention is designated by the accompanying claims and is not restricted by the descriptions of the specific embodiments. Accordingly, all the transformations and changes within the scope of the claims are to be construed as included in the scope of the present invention.

The invention claimed is:

1. Perimeter for perimetry on an eye to be examined by presenting a stimulus at a predetermined coordinate position of a first visual field coordinate system which is set on a visual field dome, comprising:
   a memory for storing a fundus image of said eye to be examined;
   means to control display for reading said fundus image and displaying said fundus image on a monitor;
   means to set coordinate for setting a second visual field coordinate system wherein a macula lutea portion of said fundus image which is displayed on said monitor is an origin on said fundus image displayed on said monitor;
   means for provisionally determining blind spot coordinate, for provisionally determining a blind spot position on said fundus image on said second visual field coordinate system;
   means to search blind spot for searching a coordinate position of a blind spot of said eye to be examined on said first visual field coordinate system by presenting said stimulus to said eye to be examined on said visual field dome;
   means to change scale for changing a scale of said second visual field coordinate system so as to correspond said coordinate value of said blind spot of said eye to be examined on said first visual field coordinate system which is obtained by said blind spot search means and said coordinate value of said blind spot of said fundus image on said second visual field coordinate system with each other; and
   means to conduct perimetry for conducting a perimetry on said eye to be examined by presenting said stimulus on said visual field dome at a position on said first visual field coordinate system having the same coordinate value as one on said second coordinate system of a predetermined test point on said fundus image.

2. The perimeter according to claim 1, wherein further comprising a memory for storing standard blind spot position coordinate data showing positions where blind spots generally exist, and means to control search for controlling said means to search blind spot to read said standard blind spot position coordinate data from said memory and to search said blind spot at a periphery of said coordinate position which is shown in said standard blind spot position coordinate data when said blind spot search means searches said coordinate position of said blind spot on said first visual field system.

* * * * *